(12) United States Patent
Plesch et al.

(10) Patent No.: US 12,039,719 B2
(45) Date of Patent: Jul. 16, 2024

(54) SYSTEM AND METHOD FOR DETECTION AND CLASSIFICATION OF OBJECTS OF INTEREST IN MICROSCOPE IMAGES BY SUPERVISED MACHINE LEARNING

(71) Applicant: MetaSystems Hard & Software GmbH, Altlussheim (DE)

(72) Inventors: Andreas Plesch, Schwetzingen (DE); Thomas Lörch, Reilingen (DE)

(73) Assignee: MetaSystems Hard & Software GmbH, Altlussheim (DE)

(*) Notice: Subject to any disclaimer, the term of this patent is extended or adjusted under 35 U.S.C. 154(b) by 667 days.

(21) Appl. No.: 17/253,411

(22) PCT Filed: Jun. 19, 2019

(86) PCT No.: PCT/IB2019/000802
§ 371 (c)(1),
(2) Date: Dec. 17, 2020

(87) PCT Pub. No.: WO2019/243897
PCT Pub. Date: Dec. 26, 2019

(65) Prior Publication Data
US 2021/0264595 A1 Aug. 26, 2021

Related U.S. Application Data

(60) Provisional application No. 62/687,215, filed on Jun. 19, 2018.

(51) Int. Cl.
*G06T 7/00* (2017.01)
*G01N 21/64* (2006.01)
*G16B 40/30* (2019.01)

(52) U.S. Cl.
CPC ....... *G06T 7/0012* (2013.01); *G01N 21/6428* (2013.01); *G16B 40/30* (2019.02); *G01N 2021/6439* (2013.01); *G06T 2207/10056* (2013.01); *G06T 2207/20081* (2013.01);
(Continued)

(58) Field of Classification Search
CPC .... A61K 31/66; A61K 33/243; G06T 7/0012; G06T 18/41; G06T 2200/24; G06T 7/187; G06T 2207/30024; G06F 18/241; G01N 21/6428; G01N 15/1433; G01N 33/5026
See application file for complete search history.

(56) References Cited

U.S. PATENT DOCUMENTS

| | | | |
|---|---|---|---|
| 7,764,822 B2 * | 7/2010 | Ramm | G06T 7/187 382/129 |
| 8,699,776 B2 * | 4/2014 | Duschesne | A61B 5/055 600/407 |
| 9,639,660 B2 * | 5/2017 | Shin | G16B 25/00 |

(Continued)

FOREIGN PATENT DOCUMENTS

| | | |
|---|---|---|
| WO | 2014150274 A1 | 9/2014 |
| WO | 2018091486 A1 | 5/2018 |

*Primary Examiner* — Yosef Kassa
(74) *Attorney, Agent, or Firm* — Verrill Dana, LLP

(57) ABSTRACT

Methods are provided for efficient training of convoluted neural networks using computer-assisted microscope image acquisition and pre-classification of training images for biological objects of interest. The methods combine use of an automated scanning platform, on-the-fly image analysis parallel to the scanning process, and a user interface for review of the pre-classification performed by the software.

24 Claims, 1 Drawing Sheet

Magazine 10  Carrier assembly 20  Microscope with CCD camera, motorized scanning stage 30  Computer. 40

(52) U.S. Cl.
CPC .............. *G06T 2207/20084* (2013.01); *G06T 2207/30024* (2013.01)

(56) References Cited

U.S. PATENT DOCUMENTS

| | | | |
|---|---|---|---|
| 9,684,960 B2* | 6/2017 | Buzaglo | G06V 10/764 |
| 9,797,332 B2* | 10/2017 | Nakano | F02D 41/401 |
| 9,949,679 B2* | 4/2018 | Renlund | A61B 5/150282 |
| 10,037,592 B2* | 7/2018 | Kolb, V | G06T 3/40 |
| 10,255,693 B2* | 4/2019 | Smith | G06T 7/97 |
| 10,632,186 B1* | 4/2020 | Zagury | C12N 15/1132 |
| 2003/0231791 A1 | 12/2003 | Torre-Bueno et al. | |
| 2012/0076390 A1 | 3/2012 | Potts et al. | |
| 2015/0268226 A1* | 9/2015 | Bhargava | G01N 33/5091 514/789 |

* cited by examiner

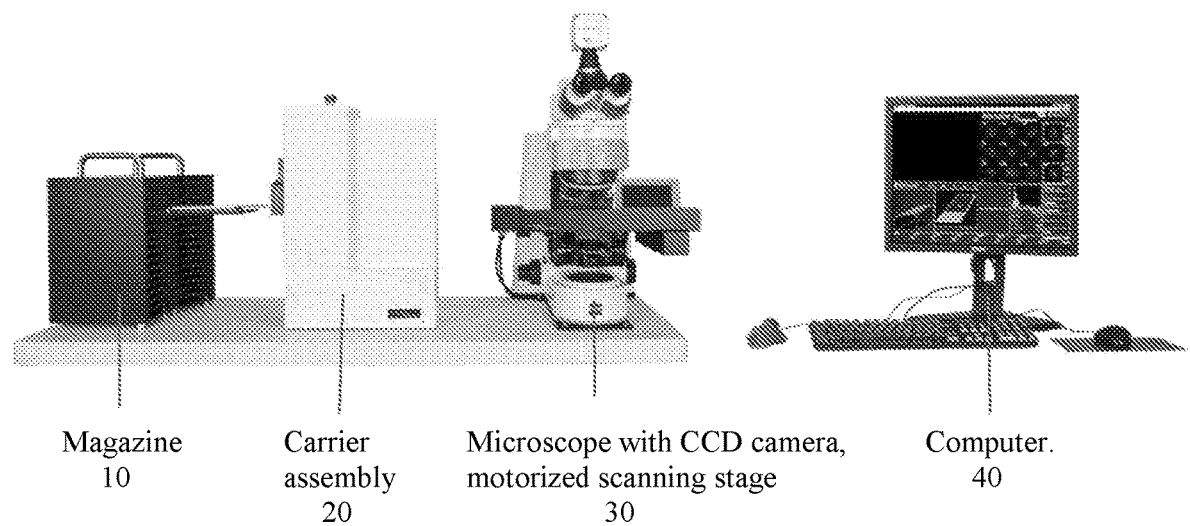
Magazine  
10
Carrier assembly  
20
Microscope with CCD camera, motorized scanning stage  
30
Computer.  
40

SYSTEM AND METHOD FOR DETECTION AND CLASSIFICATION OF OBJECTS OF INTEREST IN MICROSCOPE IMAGES BY SUPERVISED MACHINE LEARNING

BACKGROUND

Supervised machine learning methods, particularly Deep Learning (DL) using Convolutional Neural Networks (CNN) are powerful methods for the detection and classification of objects of interest in microscopic images. Deep Learning relies on tens of thousands of annotated (pre-classified) images representing regions of interest (ROI) or objects of interest (OOI) as input data to train and optimize the CNN. In addition, independent pre-classified test data sets are required to test the quality of the CNN by applying the optimized model to the test data for the assessment of the model performance, e.g. specificity and sensitivity.

There is a strong interest in automating the process of acquiring the large number of microscopic images on the one hand, and in making the pre-classification process of the ROIs as efficient and time saving as possible on the other hand.

Automatic image acquisition of microscopic images is achieved by using slide scanners. Currently available automatic slide scanners generate digital whole slide images (WSI). This process takes time as the whole slide area containing biological material is usually scanned at the target magnification. The data image data files contain gigabytes of data. Storing and handling (transferring) the huge image files require large data storage systems and powerful transmission networks, which can be expensive.

Pre-classification of images is usually performed by loading the image data files into a viewer software application. The software provides functions to navigate within the digital slide and to annotate objects of interest, e.g., by encircling them with the mouse or another appropriate input device, or by placing a frame on the image that includes the OOI, followed by assigning a class number to the OOI. This procedure requires a human expert and presents a huge workload.

Thus, there remains a need to reduce the effort required by human experts in providing training images for DL and CNN in the analysis of microscope images, as well as a need to reduce image file size and handling in such analysis.

SUMMARY

The present technology makes the training of CNNs more efficient by providing computer-assisted image acquisition and pre-classification of training images. This is achieved by the combination of an automated scanning platform, on-the-fly image analysis parallel to the scanning process, and an optimized user interface for review of the pre-classification performed by the software.

WSIs can be necessary for situations where large contiguous areas need to be imaged, such as, for instance, tissue sections in histopathology. In many situations, however, WSIs are a very inefficient way of storing the information, as the objects of interest represent a small fraction of the total image and the vast majority of pixels are background and do not carry meaningful information. The objects or regions of interest may typically correspond to only a few percent or less of the total data of a WSI. One example is blood smears, where the objects of interest may be white blood cells. Another example is aberrant cells among a large number of normal cells in liquid-based preparations in cytology. In the present technology, the use of WSIs is avoided and replaced by a two-step process involving a low magnification pre-scan and candidate detection, followed by high magnification capture of the detected candidates. This approach is particularly useful for detecting and imaging rare objects, where the average number of OOI per field of view is low. Due to the limited number of OOI images which have to be captured using this two-step approach, more sophisticated capture procedures, such as maximum precision focusing, focus stack acquisition and storage, and the like can be performed with minimal reduction of speed and throughput.

One aspect of the technology is a method for generating training images from microscope slides for use in optimizing a supervised machine learning model. The method includes the steps of: (a) performing a pre-scan of a microscope slide containing a biological specimen using a first imaging modality; (b) extracting one or more specimen features from the pre-scan; (c) identifying from the extracted specimen features one or more slide positions that are likely to contain biological objects of interest; (d) acquiring targeted images using a second, different imaging modality at said one or more slide positions; and optionally (e) presenting the acquired targeted images to a user for interactive classification of the biological objects of interest. The classified acquired targeted images are suitable for use as training images for the supervised machine learning model.

The first and second imaging modalities can differ in magnification or contrast, or can use different optical methods, such as methods selected from brightfield illumination, fluorescence microscopy, phase contrast microscopy, darkfield illumination, and differential interference contrast microscopy or other known microscopy techniques.

The extracted specimen features can include cell density, and the slide positions for image acquisition in (d) can be selected based on a pre-determined cell density. The extracted specimen features can include the presence of a pre-determined cell type, and the images acquired in (d) can contain the pre-determined cell type.

One or more brightfield stains can be applied to the biological specimen, and steps (a) through (c) can be performed using brightfield illumination as the first imaging modality, after which one or more fluorescent stains can be applied to the biological specimen and step (d) can be performed using fluorescence microscopy as the second imaging modality. A slide positioning device can automatically relocate the slide after application of the one or more fluorescent stains to a slide position identified in step (c) as likely to contain a biological object of interest.

One or more fluorescent stains can be applied to the sample and steps (a) through (c) can be performed using fluorescence microscopy as the first imaging modality, after which the one or more fluorescent stains are removed and one or more brightfield stains are applied, and step (d) is performed using brightfield illumination as the second imaging modality. A slide positioning device can automatically relocate the slide after application of the one or more brightfield stains to a slide position identified in step (c) as likely to contain a biological object of interest.

Biological objects of interest can be identified and classified in step (c) based on information from one or more fluorescent stains, and in step (d) brightfield images can be obtained of the classified biological objects of interest. The classified brightfield images can be suitable to serve as training images for a supervised machine learning process, and step (e) can be omitted. Or, step (e) can be performed, whereby an interactive correction of the classification results obtained in step (c) is made.

The identifying of step (c) and/or the classification of step (e) can include the use of a convolutional neural network. Step (b) can include applying a convolutional neural network. Step (b) can include intensity thresholding followed by size and/or shape analysis. Step (b) can include detection of a stain for a biomarker applied simultaneously with a brightfield stain.

Another aspect of the technology is a method for generation of training images from microscope slides for optimizing a supervised machine learning model. The method includes the steps of: (a) performing a pre-scan of a microscope slide containing a biological specimen using a first imaging modality and/or first staining; (b) extracting one or more specimen features from the pre-scan; (c) repeating steps (a) and (b) using a second, different imaging modality and/or second staining of the biological specimen to obtain further extracted specimen features from the repeated scan; (d) using a convolutional neural network, and the extracted specimen features of (b), and the further extracted specimen features of (c) to identify and/or classify biological objects of interest in the biological specimen; and optionally (e) presenting images of the biological objects of interest in a gallery for review and/or interactive correction by a user of the classification. The classified biological objects of interest are suitable for use as training images for the supervised machine learning model.

The biological object of interest can be, for example, a blood cell, an immune cell, a bacterium, or a parasite. The biological specimen can include a bodily fluid or cell or tissue sample of a human or animal patient. Pathological bacteria can be identified and/or classified in the biological specimen using any of the above described methods. A Gram stain can be applied before step (a) or between steps (c) and (d).

Yet another aspect of the technology is a system for the identification and/or classification of biological objects of interest on a microscope slide containing a specimen. The system can include: (a) an imaging microscope; (b) an automatic slide scanning device; (c) a computer programmed to perform any of the aforementioned methods; and (d) a machine learning model stored in the computer that has been trained using the training images generated by any of the aforementioned methods to identify and/or classify the biological objects of interest.

Still another aspect of the technology is a method for the identification and/or classification of biological objects of interest on a microscope slide. The method includes the steps of: (a) performing a pre-scan of a microscope slide using a first imaging modality and/or staining; (b) extracting one or more specimen features from the pre-scan; (c) identifying from the extracted specimen features one or more slide positions that are likely to contain biological objects of interest; (d) acquiring targeted images using a second, different imaging modality and/or staining at said one or more slide positions; and (e) using a machine learning model (CNN) to identify and/or classify biological objects of interest in the biological specimen. The method can optionally include (f) presenting images of the biological objects of interest identified in (e) to a user for review.

Evan another aspect of the technology is a method for the identification and/or classification of biological objects of interest on a microscope slide, including the steps of: (a) providing the system described above, wherein the computer contains a machine learning model that has been trained using the training images generated by any of the methods described above to identify and/or classify the biological objects of interest; (b) performing a scan of a microscope slide suspected of containing said biological objects of interest using an imaging modality and/or staining used to obtain the set of training images; (c) extracting one or more specimen features from the scan; (d) using the machine learning model to classify biological objects of interest on the slide; and optionally (e) presenting images of the biological objects of interest identified in (d) in a gallery for review by a user. Prior to step (a), the method can optionally include (a0) performing of the aforementioned methods generate a set of training images suitable for identifying or classifying the biological objects of interest and using the training images to train the machine learning model.

BRIEF DESCRIPTION OF THE DRAWINGS

FIG. 1 shows an embodiment of a microscope slide scanning and imaging system for the identification and/or classification of biological objects of interest on a microscope slide containing a specimen.

DETAILED DESCRIPTION

The present technology provides a method for generating training images from microscope slides for use in optimizing a supervised machine learning model. The method includes at least the following steps. (1) A pre-scan of a microscope slide containing a biological specimen is made using a first imaging modality (for example, a low magnification image). (2) One or more specimen features are extracted from the pre-scan image based on selected criteria. The search criteria can be selected as characteristic of, for example, a cell or tissue type, physiology, or pathology, or the presence of one or more biomarkers. Search criteria can include, for example, image features such as size, shape, stain color and/or intensity, contrast, association with neighboring structures, etc. (3) One or more slide positions are identified which are associated with the extracted specimen features and which are likely to contain biological objects of interest. (4) Targeted images are then acquired at the identified slide positions using a second imaging modality, preferably different from the first imaging modality, (for example, obtained at a higher magnification than the first, pre-scan image). (5) As an optional step, the acquired targeted images can be presented, such as in an image gallery, to a user for interactive classification of the biological objects of interest. The classified acquired targeted images are suitable for use as training images for the supervised machine learning model.

Another aspect of the technology is a method for generation of training images from microscope slides for optimizing a supervised machine learning model. The method includes the steps of: (1) performing a pre-scan of a microscope slide containing a biological specimen using a first imaging modality and/or first staining; (2) extracting one or more specimen features from the pre-scan; (3) repeating steps (1) and (2) using a second, different imaging modality and/or second staining of the biological specimen to obtain further extracted specimen features from the repeated scan (by repeating steps (1) and (2) using a different imaging modality, further information can be collected so as to allow a more refined basis for identifying specimen features for classification; (4) using the extracted specimen features of (2), and the further extracted specimen features of (3) to identify and/or classify biological objects of interest in the biological specimen; and optionally (5) presenting images of the biological objects of interest in a gallery for review and/or interactive correction by a user of the classification. The classified biological objects of interest are suitable for use as training images for the supervised machine learning model.

A further aspect of the technology is a system for the identification and/or classification of biological objects of interest on a microscope slide containing a specimen. An embodiment of the system is shown in FIG. 1, which depicts components of the Metafer system of MetaSystems GmbH. The system can include: (1) an imaging microscope (component 30 of FIG. 1); (2) an automatic slide scanning device (components 10, 20, and 30 of FIG. 1); (3) a computer programmed to perform any of the aforementioned methods; and (4) a machine learning model stored in the computer that has been trained using the training images generated by any of the aforementioned methods to identify and/or classify the biological objects of interest.

The present technology also provides a method for the identification and/or classification of biological objects of interest in a specimen on a microscope slide. The method includes the steps of: (a) performing a pre-scan of a microscope slide using a first imaging modality and/or staining; (b) extracting one or more specimen features from the pre-scan; (c) identifying from the extracted specimen features one or more slide positions that are likely to contain biological objects of interest; (d) acquiring targeted images using a second, different imaging modality and/or staining at said one or more slide positions; and (e) using a machine learning model (CNN) to identify and/or classify biological objects of interest in the biological specimen. The method can optionally include (f) presenting images of the biological objects of interest identified in (e) to a user for review.

Another method according to the present technology can be used for the identification and/or classification of biological objects of interest on a microscope slide. The method includes the steps of: (a) providing the slide scanning and imaging system described above, wherein the computer contains a machine learning model that has been trained using the training images generated by any of the methods described above to identify and/or classify the biological objects of interest; (b) performing a scan of a microscope slide suspected of containing said biological objects of interest using an imaging modality and/or staining used to obtain the set of training images; (c) extracting one or more specimen features from the scan; (d) using the machine learning model to classify biological objects of interest on the slide; and optionally (e) presenting images of the biological objects of interest identified in (d) in a gallery for review by a user. Prior to step (a), the method can optionally include (a0) performing of the aforementioned methods generate a set of training images suitable for identifying or classifying the biological objects of interest and using the training images to train the machine learning model.

The following describes some aspects of the present technology that take advantage of the features of an automated scanning platform.

Overview Scan and Sample Density Optimization

Smear preparations often show a decreasing density of cells/biological material along the length of the smear. After doing a low magnification overview scan of the slide, the region with the most appropriate cell density can be determined by image analysis, and the subsequent scan with high magnification can be limited to the most promising areas of the specimen. This procedure assures that regions will be imaged that have a sufficient information density without exhibiting excessive cell overlaps or clumps. Likewise, areas with obvious artifacts like air bubbles, scratches, dust, etc. can be automatically detected and can be avoided.

Overview Scan and Field-of-View Optimization

In this embodiment, the scanning platform scans the slide at a first low magnification to provide an overview image. During the scan, the software detects OOI (e.g., white blood cells on a blood smear). After the pre-scan, the software analyzes the distribution of the detected OOI and determines the number and position of images to be captured at the second, higher magnification that will yield the required number of OOI with a minimum of captured images (field of view optimization). This procedure assures a minimum of scan time, data volume and storage space, and user interaction for review.

Object Detection and Gallery Creation

In this embodiment, the slide is scanned, and the software detects OOI during the scan. Detected OOI are presented in a gallery for subsequent review. An optimized user interface and workflow assure pre-classification by the expert within a minimum of time (rapid score). The user is alerted by the software when the required number of objects per class or total objects has been pre-classified.

Automatic Pre-Classification During the Scan

An additional time gain is achieved if the software not only detects OOI during the scan, but already provides a pre-classification to put the detected OOI in their respective bins. The user interaction during review of the pre-classified training data will then be reduced to correcting only the misclassified OOI. This workflow will be helpful if a classification model already exists but needs to be improved by generating more training data, or if pre-classification by feature transfer (see below) is to be performed. Implementing a stop condition, e.g., once the required number of OOI has been detected, assures minimum scan time and maximum throughput.

Pre-Classification by Feature Transfer

Pre-classification can be automated if the OOI that are to be detected in brightfield images can be labeled in an additional image channel by applying a fluorescent biomarker. The standard stain will be stored in the R-, G-, B-channels, while the fluorescence information is stored in a separate image channel. Automatic identification of the biomarker in the extra channel is easily possible and allows for reliable pre-classification of the OOI. The subsequent training/optimization is performed based on the RGB-channels of the training images. An example is using a $p16^{ink}$ antibody, labeled with a fluorophore, to detect pre-cancerous or cancerous cervical cells in a Pap smear preparation. Using an additional biomarker, e.g., the proliferation marker Ki67 labeled with a second fluorophore acquired into a $5^{th}$ color channel, is easily possible (see, e.g., Roche CINtec assay).

Another example is the use of the dual fluorescent stain using hexidium iodide (HI) and SYTO 13 to differentially label Gram-positive and Gram-negative bacteria (U.S. Pat. No. 4,665,024). Fluorescently labeled objects are easier to detect and to distinguish by image analysis, which helps to automate the pre-classification of Gram stain bacteria. Additionally, the dual fluorescent stain can reduce the inherent ambiguities of the Gram stain.

Other biomarkers such as FISH probes (DNA, RNA, etc.) may be used. Fluorescent DNA probes detecting bacterial rRNA may be used to detect and classify bacteria, e.g., in Gram stain preparations or to differentiate parasites like plasmodia in Malaria diagnosis.

In situations where the brightfield stain and the additional biomarker label cannot be applied simultaneously to the sample, an automated slide scanner such as the Metafer platform can provide a highly precise relocation function even after removing the specimen and destaining and restaining it with the second dye or biomarker. The image data acquired during the two scans can be merged in one file or linked together for analysis/review. More efficiently, the biomarker could be applied and scanned first, biomarker-positive OOI could be detected automatically, and the scan after destaining/restaining would be limited to acquiring images at the positions of the previously detected OOI.

Detecting the biomarker can be done at low magnification, particularly if a fluorescent antibody is used that labels large cell compartments like nucleus or cytoplasm. A position list of detected OOI can be generated. The brightfield (morphological) images requiring higher magnification can be captured after relocating to the coordinates stored in the position list.

Dual Magnification Scan and Review

CNN have the potential to successfully classify low quality images that human experts have difficulty to interpret. This can be used to make the image acquisition more efficient, e.g., by scanning with a reduced magnification, at reduced exposure time/reduced signal-to-noise ratio, with imperfect focusing, with a lower aperture (dry) objective, etc. The CNN can use these lower quality images to perform the object classification. The expert review, however, will generally require high quality images. To facilitate this, OOI detected by the CNN at lower magnification can be additionally acquired at higher magnification or using a high N.A. immersion lens and be presented to the human expert for review and confirmation. This workflow can be particularly interesting in rare object situations. High magnification review images of the detected OOI may comprise several focus planes to facilitate expert review. Compared to multiple focus plane imaging of the whole scan area this targeted approach saves a huge amount of time and data storage.

Alternative to acquiring high resolution review images of the detected OOI, microscope-based review is equally possible. The system can automatically relocate any detected OOI under the microscope for direct review. Having full manual control of the microscope for review can be an advantage over digital image review. To assure precise relocation of previously detected OOI the system needs to be calibrated in a way that the OOI are presented in the center of the microscopic field of view irrespective of the specimen position in the specimen holder and of the position of the specimen holder in the slide loader magazine (see U.S. Pat. No. 9,243,934).

Description of Metafer Scanning Platform

The Metafer scanning platform consists of a motorized microscope (Carl Zeiss Axiolmager.Z2), a motorized scanning stage (Maerzhaeuser), a digital camera (MetaSystems), a personal computer for system control and image analysis, and a slide loader robot with several magazines. Specimens are usually put on standard glass slides of 1" by 3". Typically, 5 slides are held in one slide holder. Each magazine holds 16 slide holders. Up to 10 magazines are supported, enabling unattended scanning of up to 800 slides. Other holders for non-standard slide formats, such as 2" by 3" slides or microwell plates, are available.

When a slide holder is loaded from the magazine, it is first transported to a bar code reader where the holder barcode as well as the individual slide barcodes are read. The slide barcodes refer to data files that define the scanning action to be taken for each individual slide. Next, the slide holder is put on the scanning stage and the scan starts.

Metafer can also be run without a slide feeder system. In this case, the slide holder is put manually on the scanning stage, and the barcode is read using a handheld scanner or is imaged through a low power microscope objective and analysed by the Metafer software. Manual set up of the scan parameters is possible as an alternative to barcodes.

The first step of the scan is a grid focus analysis. At a prefined number of grid positions within the scan area, the plane of best focus is detected, and an interpolated focus surface of the sample is calculated. During the actual scan, the system will automatically follow this predetermined focus surface. This grid focus procedure is usually performed using a low power lens with, e.g., 5× or 10× magnification that is suitable for a pre-scan or overview scan. The precision of the grid focus surface is sufficient for image analysis and OOI detection. Detected OOI, e.g., cells, can be displayed as thumbnail images in a gallery, and their coordinates can be stored in a position list. The scan continues until a preset number of OOI have been detected or until the scan area has been completely scanned.

Alternatively, the overview scan can be used to detect the slide area containing biological material. This can be achieved by analyzing the optical density of each image and comparing it to a threshold to differentiate empty areas from material. Another requirement may be to detect a slide region with suitable specimen density, e.g., when analyzing blood smears. Other criteria can be used as well to detect suitable areas or suitable object candidates.

In most applications, high quality images of the OOI are required for review or for using them as training data for supervised machine learning approaches. To capture high quality images, the system will, in a next step, change the objective lens and apply immersion oil if necessary.

Based on the previously generated position list, high magnification images are captured. As the initial course grid focus is not sufficient to assure perfect focusing of high aperture lenses with their reduced depth of field (compared to the relatively high depth of field of the low magnification, low numerical aperture lens used for the prescan), each individual high magnification image needs to be refocused. Depending on the scan requirement, the OOI density, etc., individual images are taken for each detected OOI with the individual OOI centered in the field of view of the camera or the system can calculate image positions to capture a predetermined number of OOI with a minimum of individual field of view images. The latter approach will save time if the OOI density is high enough that individual field of view images may comprise more than a single OOI. Often it is advantageous to capture images at different focus planes and to store these images for later review or to use them in order to create an extended focus image that is composed of the in-focus information of each pixel position.

These images can be stored for later review or analysis, or they can be analysed on the fly and parallel to the scan process.

Example 1. White Blood Cell (WBC) Classification

In this example, white blood cells contained in a blood smear slide are captured and pre-classified into several sub-groups, such as lymphocytes, neutrophils, basophils, eosinophils, and monocytes.

A typical number of white blood cells to be captured is 500 per slide.

With a given Metafer configuration, the combination of a 12 MPixel camera having a 3.45 µm pixel size (MetaSystems CoolCube4) and a 20× objective is required to achieve images with sufficient detail. The approach prior to the present technology would be to scan the scan area (which can be a predefined area on the slide or the smear as detected during a low magnification prescan) at 20× magnification and would generate a digital image of the scan area. Assuming a scan area of 10 mm×10 mm, the resulting image will have an uncompressed size of approx. 10 GB.

According to the technology, the scanning platform performs an overview scan at 5× magnification, which takes about 20 seconds. During the scan, white blood cells are detected and their positions are recorded. For a typical density of white blood cells, the field-of-view-optimisation software will identify 100 or fewer positions to assure that the required 500 WBCs are captured at the target magnification of 20×. The captured WBCs are stored as individual thumbnail images of 244×244 pixels, corresponding to 180 kB of data (again uncompressed). Compared to the conventional scenario of the prior art, the data reduction is 10,000,000/(500×180)=111-fold.

The time required for image acquisition corresponds roughly to the same factor of 100-fold reduction.

To estimate the time gain for pre-classification of 500 WBCs we need to compare the conventional approach of manually annotating the WBCs within a virtual slide viewer software with the gallery-based rapid review. With the conventional "virtual slide" approach the operator performs the following interactions: navigating within the image (zoom, pan and scroll), positioning a square of pre-defined size over the WBCs and selecting an object class by typing a number or clicking on a checkbox. These operations will take approx. 5 seconds on the average.

The gallery-based approach does not require any navigation within an image or any mouse movements: a gallery object is identified and upon typing its class number on the scoring keypad the software selects the next gallery object for review. The interaction is reduced to one click. An experienced operator is only limited by the time it takes him to recognize the WBC. A classification rate of 1 to 2 per second is easily achievable. In addition to the time savings there is a significant reduction of operator stress due to eliminating excessive mouse operations.

An additional time savings is achieved if the WBCs are automatically pre-classified by the software. Either a simple feature based classifier or a known CNN that needs to be further optimized can be used for the classification. In this case, the gallery can be filtered to display only WBCs of a particular class. The review of the filtered gallery and the rejection or reclassification of misclassified objects is significantly faster compared to a random object gallery.

Example 2. WBC Automatic Pre-Classification by "Feature Transfer" Between Different Image Channels/Staining Conditions Pre-classification of WBC requires a person with expertise to inspect the cell morphology. By means of antibodies that are specific with respect to the individual WBC populations, morphology classification can be replaced with antibody detection. To this end, the WBC are either simultaneously or sequentially labeled with the fluorescent antibody and the brightfield stain. Optionally, multiple antibodies that are labeled with separate fluorochromes (multiplex labeling) can be used to label the cells simultaneously. The scanning platform is able to merge the information and to classify the WBC based on their antibody-positivity by detecting the individual fluorescent antibody labels. As the brightfield information is equally available, the pre-classified images are suitable training data for optimizing a morphology-based machine learning model.

Example 3. WBC Automatic Pre-Classification with "Feature Transfer" from Low Quality to High Quality Images Experiments have shown that CCN are capable of classifying images of lower quality (e.g., lower magnification, less perfect focussing, shorter exposure time, higher image noise, etc.) than the quality of the images used for optimizing the model. The time savings in capturing training images at low resolution, classifying them using a CNN, and recapturing the identified and pre-classified objects at a magnification that is sufficient for operator review and confirmation, is significant (at least the square of the ratio of the two magnifications). The classification result at the lower quality is still good enough to assure that the vast majority of pre-classification results are correct, and only a minority of objects need to be reclassified by the expert prior to being used as training images for optimizing the CNN.

That which is claimed is:
1. A method for generating training images from microscope slides for use in optimizing a supervised machine learning model, the method comprising the steps of:
   (a) performing a pre-scan of a microscope slide containing a biological specimen using a first imaging modality;
   (b) extracting one or more specimen features from the pre-scan;
   (c) identifying from the extracted specimen features one or more slide positions that are likely to contain biological objects of interest, wherein the extracted specimen features include cell density or cell type;
   (d) acquiring targeted images using a second, different imaging modality at said one or more slide positions selected based on a pre-determined cell density or a pre-determined cell type;
   (e) presenting the acquired targeted images for interactive classification of the biological objects of interest, wherein the classified acquired targeted images are suitable for use as training images for the supervised machine learning model.
2. The method of claim 1, wherein the first and second imaging modalities differ in magnification.
3. The method of claim 1, wherein the first and second imaging modalities differ in contrast.
4. The method of claim 1, wherein the first and second imaging modalities use different optical methods selected from the group consisting of brightfield illumination, fluorescence microscopy, phase contrast microscopy, darkfield illumination, and differential interference contrast microscopy or other well-known microscopic techniques.
5. The method of claim 1, wherein the extracted specimen features include cell density, and the slide positions for image acquisition in (d) are selected based on a pre-determined cell density.
6. The method of claim 1, wherein the extracted specimen features include presence of a pre-determined cell type, and the images acquired in (d) contain the pre-determined cell type.
7. The method of claim 1, wherein one or more brightfield stains are applied to the biological specimen and steps (a) through (c) are performed using brightfield illumination as the first imaging modality, after which one or more fluorescent stains are applied to the biological specimen and step (d) is performed using fluorescence microscopy as the second imaging modality.

8. The method of claim 7, wherein a slide positioning device automatically relocates the slide after application of the one or more fluorescent stains to a slide position identified in step (c) as likely to contain a biological object of interest.

9. The method of claim 1, wherein one or more fluorescent stains are applied to the sample and steps (a) through (c) are performed using fluorescence microscopy as the first imaging modality, after which the one or more fluorescent stains are removed and one or more brightfield stains are applied, and step (d) is performed using brightfield illumination as the second imaging modality.

10. The method of claim 9, wherein a slide positioning device automatically relocates the slide after application of the one or more brightfield stains to a slide position identified in step (c) as likely to contain a biological object of interest.

11. The method of claim 9, wherein biological objects of interest are identified and classified in step (c) based on information from the one or more fluorescent stains, and in step (d) brightfield images are obtained of the classified biological objects of interest, and wherein said classified brightfield images are suitable to serve as training images for a supervised machine learning process, and wherein step (e) is not performed; or wherein step (e) is performed, whereby an interactive correction of the classification results obtained in step (c) is made.

12. The method of any of claim 1, wherein the identifying of step (c) and/or the classification of step (e) comprises the use of a convolutional neural network.

13. The method of claim 1, wherein step (b) comprises applying a convolutional neural network.

14. The method of claim 1, wherein step (b) comprises intensity thresholding followed by size and/or shape analysis.

15. The method of claim 1, wherein step (b) comprises detection of a stain for a biomarker applied simultaneously with a brightfield stain.

16. A method for generation of training images from microscope slides for optimizing a supervised machine learning model, the method comprising the steps of:
(a) performing a pre-scan of a microscope slide containing a biological specimen using a first imaging modality and/or first staining;
(b) extracting one or more specimen features from the pre-scan, wherein the specimen features include cell density or cell type;
(c) repeating steps (a) and (b) using a second, different imaging modality and/or second staining of the biological specimen to obtain further extracted specimen features from the repeated scan;
(d) using a convolutional neural network, the extracted specimen features of (b), and the further extracted specimen features of (c) to identify and/or classify biological objects of interest in the biological specimen; and optionally
(e) presenting images of the biological objects of interest in a gallery for review and/or interactive correction of the classification;
wherein the classified biological objects of interest are suitable for use as training images for the supervised machine learning model.

17. The method of claim 1, wherein the biological object of interest is a blood cell, an immune cell, a bacterium, or a parasite.

18. The method of claim 1, wherein the biological specimen comprises a bodily fluid or cell or tissue sample of a human or animal patient.

19. The method of claim 17, wherein pathological bacteria are identified and/or classified in the biological specimen.

20. The method of claim 19, wherein a Gram stain is applied before step (a) or between steps (c) and (d).

21. A system for the identification and/or classification of biological objects of interest on a microscope slide containing a specimen, the system comprising
(a) an imaging microscope;
(b) an automatic slide scanning device;
(c) a computer programmed with a machine learning model for the identification and/or classification of biological objects of interest on a microscope slide containing a specimen,
wherein the machine learning model has been trained to identify and/or classify the biological objects of interest by a method comprising the steps of:
(i) performing a pre-scan of a microscope slide containing a biological specimen using a first imaging modality;
(ii) extracting one or more specimen features from the pre-scan;
(iii) identifying from the extracted specimen features one or more slide positions that are likely to contain biological objects of interest;
(iv) acquiring targeted images using a second, different imaging modality at said one or more slide positions; and
(v) presenting the acquired targeted images for interactive classification of the biological objects of interest, wherein the classified acquired targeted images are suitable for use as training images for the supervised machine learning model.

22. A method for the identification and/or classification of biological objects of interest on a microscope slide, the method comprising the steps of:
(a) performing a pre-scan of a microscope slide using a first imaging modality and/or staining;
(b) extracting one or more specimen features from the pre-scan, wherein the specimen features include cell density or cell type;
(c) identifying from the extracted specimen features one or more slide positions that are likely to contain biological objects of interest;
(d) acquiring targeted images using a second, different imaging modality and/or staining at said one or more slide positions; and
(e) using a machine learning model (CNN) to identify and/or classify biological objects of interest in the biological specimen; and optionally
(f) presenting images of the biological objects of interest identified in (e) for review.

23. A method for the identification and/or classification of biological objects of interest on a microscope slide, the method comprising the steps of:
(a) providing a system comprising an imaging microscope, an automatic slide scanning device, and a computer, wherein the computer contains a machine learning model that has been trained using training images generated by a method to identify and/or classify the biological objects of interest, the method comprising the steps of:

(i) performing a pre-scan of a microscope slide containing a biological specimen using a first imaging modality;
(ii) extracting one or more specimen features from the pre-scan;
(iii) identifying from the extracted specimen features one or more slide positions that are likely to contain biological objects of interest;
(iv) acquiring targeted images using a second, different imaging modality at said one or more slide positions;
(v) presenting the acquired targeted images for interactive classification of the biological objects of interest, wherein the classified acquired targeted images are suitable for use as training images for the supervised machine learning model;

(b) performing a scan of a microscope slide suspected of containing said biological objects of interest using an imaging modality and/or staining used to obtain the set of training images;
(c) extracting one or more specimen features from the scan;
(d) using said machine learning model to classify biological objects of interest on the slide; and optionally
(e) presenting images of the biological objects of interest identified in (d) in a gallery for review.

24. The method of claim 23, further comprising the step of, prior to step (a):
(a0) performing a method comprising the steps of:
(i) performing a pre-scan of a microscope slide containing a biological specimen using a first imaging modality;
(ii) extracting one or more specimen features from the pre-scan;
(iii) identifying from the extracted specimen features one or more slide positions that are likely to contain biological objects of interest;
(iv) acquiring targeted images using a second, different imaging modality at said one or more slide positions;
(v) presenting the acquired targeted images for interactive classification of the biological objects of interest;

thereby generating a set of training images suitable for identifying or classifying the biological objects of interest and using the training images to train the machine learning model.

* * * * *